(12) United States Patent
Weiss et al.

(10) Patent No.: US 6,844,312 B2
(45) Date of Patent: Jan. 18, 2005

(54) PRODUCTION OF TYROSINE HYDROXYLASE POSITIVE NEURONS

(75) Inventors: Samuel Weiss, Calgary (CA); Tetsuro Shingo, Okayama (JP)

(73) Assignee: Stem Cell Therapeutics Inc., Calgary (CA)

( * ) Notice: Subject to any disclaimer, the term of this patent is extended or adjusted under 35 U.S.C. 154(b) by 2 days.

(21) Appl. No.: 10/118,167

(22) Filed: Apr. 9, 2002

(65) Prior Publication Data

US 2002/0192817 A1 Dec. 19, 2002

Related U.S. Application Data

(60) Provisional application No. 60/282,918, filed on Apr. 11, 2001.

(51) Int. Cl.$^7$ .......................... A61K 31/00; A61K 38/00
(52) U.S. Cl. ............................................... 514/1; 514/2
(58) Field of Search ......................... 514/1, 2; 530/300, 530/399

(56) References Cited

U.S. PATENT DOCUMENTS

| | | | |
|---|---|---|---|
| 5,750,376 A | 5/1998 | Weiss et al. | |
| 5,851,832 A | 12/1998 | Weiss et al. | |
| 5,980,885 A | 11/1999 | Weiss et al. | |
| 5,981,165 A | 11/1999 | Weiss et al. | |
| 6,040,180 A | * 3/2000 | Johe | ........................... 435/377 |

OTHER PUBLICATIONS

Klint & Claesson–Welsh (Feb. 15, 1999) "Signal transduction by fibroblast growth factor receptors." Front Biosci. 4: D165–7.*

Du Xinyu et al., "Brain–derived neurotrophic factor works coordinately with partner molecules to initiate tyrosine hydroxylase expression in striatal neurons", Brain Research, 680:229–233 (1995).

Shingo, T. et al., ABSTRACT, "Robust induction of tyrosine hydroxylase in embryonic and adult striatal neural stem cell–derived nerons in defined media and the absence of gene transfer", Database Biosis "Online", accession No. PREV200100088076 XP002203151, Society for Neuroscience Abstract, vol. 26, No. 1–2:312.18 (2000).

Zheng, G., et al., "Regulation of tyrosine hydroxylase gene expression during transdifferentiation of striatal neurons: Changes in transcription factors binding the AP–a site", Journal of Neuroscience 18:8163–8174 (1998).

Du et al., "Multiple signaling pathways direct the initiation of tyrosine hydroxylase gene expression in cultured brain neurons," Molecular Brain Research 50: 1–8 (1997a).

Du et al., "Protein Kinase C Activators Work in Synergy with Specific Growth Factors to Initiate Hydroxylase Expression in Striatal Neurons in Culture," J. Neurochemistry, 68: 654–569 (1997b).

Du et al., "Synergy between Growth Factors and Transmitters Required for Catecholamine Differentiation in Brain Neurons," J. Neuroscience, 15: 5420–5427 (1995).

Du et al., "Novel expression of the tryosine hydroxylase gene requires both acidic fibroblast growth factor and an activator," J. Neuroscience, 14: 7688–7694 (1994).

Iacovitti et al., "Expression of tryosine hydroxylase in newly differentiated neurons from a human cell line (hNT)," NeuroReport, 8: 147–1474 (1997).

Ling et al., "Differentiation of Mesencephalic Progenitor Cells into Dopaminergic Neurons by Cytokines," Experimental Neurology, 149: 411–423 (1998).

Marsden et al., "Success and problems of long–term levodopa therapy in Parkinson's disease," Lancet 1(8007):345–9 (1977).

Max et al., "Co–expression of tyrosine hydroxylase and glutamic acid decarboxylase in dopamine differentiation factor–treated striatal neurons in culture," Developmental Brain Research, 91: 140–142 (1996).

Stull et al., "Acidic Fibroblast Growth Factor and Catecholamines Synergistically Up–Regulate Tyrosine Hydroxylase Activity in Developing and Damaged Dopamine Neurons in Culture," J. Neurochemistry, 67 : 1619–1524 (1996).

von Voigtlander, P.F. and Moore, K.E., "Turning behavior of mice with unilateral 6–hydroxydopamine lesions in the striatum: effects of apomorphine, L–DOPA, amantadine, amphetamine and other psychomotor stimulants," Neuropharmacology, 12: 451–462 (1972).

* cited by examiner

Primary Examiner—Elizabeth C. Kemmerer
Assistant Examiner—Christopher James Nichols
(74) Attorney, Agent, or Firm—Fish & Richardson P.C.

(57) ABSTRACT

The present invention relates to a method of producing neurons that express the enzyme tyrosine hydroxylase (TH) by subjecting neural stem cells to FGF-1, a protein kinase A activator, a protein kinase C activator, and dopamine/L-DOPA. Surprisingly, when forskolin is used as a protein kinase A activator, it requires only low levels of FGF-1 and forskolin to efficiently produce TH positive neurons from fetal or adult neural stem cells. Also provided are compositions used to produce TH positive neurons and the resulting neural cell culture, as well as a method of treating disease or conditions which are associated with dopamine neuron loss or dysfunction.

38 Claims, No Drawings

PRODUCTION OF TYROSINE HYDROXYLASE POSITIVE NEURONS

RELATED APPLICATION

This application claims the benefit of U.S. Provisional Application Ser. No. 60/282,918, filed Apr. 11, 2001, which is hereby incorporated by reference in its entirety.

FIELD OF THE INVENTION

The present invention relates to methods of producing neurons which express the enzyme tyrosine hydroxylase, including dopamine neurons.
References Du et al., "Multiple signaling pathways direct the initiation of tyrosine hydroxylase gene expression in cultured brain neurons", *Molecular Brain Research* 50: 1–8 (1997a).

Du et al., "Protein Kinase C Activators Work in Synergy with Specific Growth Factors to Initiate Hydroxylase Expression in Striatal Neurons in Culture", *J. Neurochemistry*, 68: 654–569 (1997b).

Du et al., "Synergy between Growth Factors and Transmitters Required for Catecholamine Differentiation in Brain Neurons", *J. Neuroscience*, 15: 5420–5427 (1995).

Du et al., "Novel expression of the tyrosine hydroxylase gene requires both acidic fibroblast growth factor and an activator", *J. Neuroscience*, 14: 7688–7694 (1994).

Lacovitti et al., "Expression of tyrosine hydroxylase in newly differentiated neurons from a human cell line (hNT)", *NeuroReport*, 8: 147–1474 (1997).

Ling et al., "Differentiation of Mesencephalic Progenitor Cells into Dopaminergic Neurons by Cytokines", *Experimental Neurology*, 149: 411–423 (1998).

Marsden et al., "Success and problems of long-term levodopa therapy in Parkinson's disease", *Lancet* 1(8007) :345–9 (1977).

Max et al., "Co-expression of tyrosine hydroxylase and glutamic acid decarboxylase in dopamine differentiation factor-treated striatal neurons in culture", *Developmental Brain Research*, 91: 140–142 (1996).

*Remington's Pharmaceutical Sciences.* Mace Publishing Company, Philadelphia Pa. $19^{th}$ ed. (1995).

Stull et al., "Acidic Fibroblast Growth Factor and Catecholamines Synergistically Up-Regulate Tyrosine Hydroxylase Activity in Developing and Damaged Dopamine Neurons in Culture", *J. Neurochemistry*, 67: 1619–1524 (1996).

von Voigtlander, P. F. and Moore, K. E., "Turning behavior of mice with unilateral 6-hydroxydopamine lesions in the striatum: effects of apomorphine, L-DOPA, amantadine, amphetamine and other psychomotor stimulants", *Neuropharmacology*, 12: 451–462(1972).

U.S. Pat. No. 5,750,376.
U.S. Pat. No. 5,980,885.
U.S. Pat. No. 5,851,832.

All of the above publications, patents and patent applications are herein incorporated by reference in their entirety to the same extent as if the disclosure of each individual publication, patent application or patent was specifically and individually indicated to be incorporated by reference in its entirety.

BACKGROUND OF THE INVENTION

Tyrosine hydroxylase (TH) is the first and rate-limiting enzyme in the biosynthesis pathway of the catecholamine neurotransmitters: dopamine, epinephrine and norepinephrine. These neurotransmitters are among the most widely used and universally distributed neurochemical systems in the brain. Imbalances in brain catecholamine levels are associated with several diseases such as Alzheimer's disease, Parkinson's disease, Tourette's syndrome, schizophrenia, and clinical depression (Stull et al., 1996). Because the brain catecholamine levels are directly related to levels of biosynthesis of catecholamines, it is useful to produce neurons which express the rate limiting enzyme in catecholamine biosynthesis, TH. These TH positive neurons can be transplanted into catecholamine deficient patients to provide catecholamines, and they are also useful in the studies of catecholamine biosynthesis and neuronal differentiation.

For example, Parkinson's disease is an age-related disorder characterized by a loss of dopamine neurons in the substantia-nigra of the midbrain, which normally send signals to the basal ganglia using dopamine as the neurotransmitter. The symptoms of Parkinson's disease include tremor, rigidity and ataxia. The disease is progressive but can be treated by administration of pharmacological doses of the precursor for dopamine, L-DOPA. However, with chronic use of pharmacotherapy the patients often become refractory to the continued effect of L-DOPA (Marsden et al., 1977). There are many suggested mechanisms for the development of the refractory state, but the simplest is that the patients reach a threshold of cell loss, wherein the remaining cells cannot synthesize sufficient dopamine from the dopamine precursor. At this stage, TH positive neurons could be transplanted into the patient to compensate for the cell loss.

Since neurons are not capable of replicating, it is not practical to generate the required quantity of TH expressing neurons by culturing neurons in vitro. A good approach would be to culture a precursor cell which can replicate and produce neurons in vitro. Ideally, the precursor cells will proliferate or differentiate in response to different signals such that one can control the quantity and timing of neuron production.

Multipotent neural stem cells are an ideal precursor cell for this purpose. Methods of isolating and culturing multipotent neural stem cells in vitro have previously been developed (for example see U.S. Pat. Nos. 5,750,376; 5,980,885; 5,851,832). Briefly, these stem cells may be isolated from both fetal and adult brains, and cultured in vitro indefinitely. These cells retain the ability to proliferate in response to growth factors, or differentiate into all lineages of neural cells (neurons and glia cells, including astrocytes and oligodendrocytes) in response to differentiation stimuli. These cells thus provide an excellent source of neuron production as well as a model system for the study of regulatory mechanisms for neuron production.

Alternatively, it is also desirable to produce TH positive neurons in vivo to compensate for lost or dysfunctional neurons. Accordingly, the need exists for methods of producing TH positive neurons in vitro and in vivo.

SUMMARY OF THE INVENTION

In the present invention, we developed a method of producing tyrosine hydroxylase (TH) positive neurons from neural stem cells. TH neurons were produced from neural stem cells using a culture medium containing fibroblast growth factor 1 (FGF-1), isobutylmethylxanthine (IBMX), forskolin, phorbol 12-myristate 13-acetate (PMA), and dopamine. Surprisingly, even with low concentrations of FGF-1, IBMX and forskolin (0.2 ng/ml FGF-1, 40 µM IBMX and 1 µM forskolin), this culture medium induced production of as much as 45% TH positive neurons in all neurons produced from neural stem cells. We also demonstrated that neural stem cells from both embryonic and adult brains can produce TH positive neurons. In addition, other protein kinase A activators or protein kinase C activators can also be used in the place of or in addition to IBMX, forskolin and PMA.

Accordingly, one aspect of the present invention provides a method for producing tyrosine hydroxylase (TH) positive neurons from neural stem cells, comprising:

(a) providing at least one mammalian non-embryonic neural stem cell;

(b) contacting the neural stem cell with an effective amount of fibroblast growth factor 1 (FGF-1), a protein kinase A activator, a protein kinase C activator, and dopamine/L-DOPA; and (c) allowing the neural stem cell to differentiate into TH positive neurons.

It is contemplated that other fibroblast growth factors, such as FGF-2, can also be used in lieu of or in addition to FGF-1 in the methods and compositions of the present invention.

The protein kinase A activator in the present invention may be any protein kinase A activator or combination thereof, and is preferably selected from the group consisting of isobutylmethylxanthine (IBMX), pituitary adenylate cyclase activating polypeptide (PACAP), forskolin, and any combination thereof.

The protein kinase C activator in the present invention may be any protein kinase C activator or combination thereof. It is preferably a phorbol ester. A number of phorbol esters are known to activate protein kinase C and can be used in the present invention, including phorbol 12-myristate 13-acetate (PMA), 4-β-12-O-tetradecanoylphorbol 13-acetate (TPA), phorbol 12,13-dibutyrate, and phorbol 12,13-diacetate. The preferred phorbol ester is PMA or TPA. However, it is also contemplated that other protein kinase C activators, either a phorbol ester or not, can be included in the present invention.

This method can be applied in vitro or in vivo. For example, the neural stem cell may be provided as a culture derived from the subventricular zone of an adult brain, and step (b) comprises contacting the culture with a TH culture medium comprising FGF-1, a protein kinase A activator, a protein kinase C activator, and dopamine/L-DOPA. Alternatively, the neural stem cell may be located in the brain of a mammal.

Optionally, the neural stem cells can be further contacted with epidermal growth factor (EGF) and/or bone morphogenic protein 2 (BMP-2) and/or brain-derived neurotrophic factor (BDNF). However, BMP-2, or any other transforming growth factor beta family member, can be omitted. Transforming growth factor beta family members include, for example, transforming growth factors beta, basic myelin proteins (BMP-2, BMP-4, BMP-5, BMP-6, BMP-7), activins A and B, decapentaplegic (dpp), 60A, OP-2, dorsalin, GDFs (1, 3, and 9), nodal, MIS, Inhibin alpha, and glial-derived neurotrophic factor (GDNF)

Another aspect of the present invention provides a method for producing tyrosine hydroxylase (TH) positive neurons from neural stem cells in vitro, comprising:

(a) providing a culture of neural stem cells;

(b) incubating the neural stem cells in a TH culture medium comprising an effective concentration of fibroblast growth factor 1 (FGF-1), a protein kinase A activator, a protein kinase C activator and dopamine/L-DOPA, with the proviso that if the neural stem cells are embryonic neural stem cells and the protein kinase A activator is a combination of isobutylmethylxanthine (IBMX) and forskolin, the concentration of forskolin is less than about 3 μM; and (c) allowing the neural stem cells to produce TH positive neurons.

When the protein kinase A activator is a combination of IBMX and forskolin, the concentration of forskolin is preferably about 2 μM and more preferably about 1 μM.

FGF-1 can be included at any effective concentration. Preferably, FGF-1 concentration in the culture medium is less than about 1 ng/ml. More preferably, the concentration of FGF-1 is about 0.2 ng/ml. IBMX can be included at any effective concentration, and the preferred concentration is less than about 50 μM, more preferably about 40 μM.

The TH culture medium can further comprise bone morphogenic protein 2 (BMP-2), brain-derived neurotrophic factor (BDNF), epidermal growth factor (EGF) and/or fibroblast growth factor 2 (FGF-2). Preferably BMP-2 is included, and more preferably both BMP-2 and BDNF are included.

In order to prolong the presence of TH positive neurons in the culture, the TH culture medium is preferably replenished regularly with fresh medium. In a preferred embodiment, at least half of the culture medium is replaced daily with an equal volume of fresh TH culture medium.

Yet another aspect of the present invention provides a composition useful for producing TH positive neurons from neural stem cells, comprising fibroblast growth factor 1 (FGF-1), a protein kinase A activator, a protein kinase C activator, and dopamine/L-DOPA, with the proviso that if the protein kinase A activator is a combination of isobutylmethylxanthine (IBMX) and forskolin, the concentration of forskolin is less than about 3 μM. When the protein kinase A activator is a combination of IBMX and forskolin, the concentration of forskolin is preferably about 2 μM and more preferably about 1 μM.

FGF-1 can be included in this composition at any effective concentration. Preferably, FGF-1 concentration in the culture medium is less than about 1 ng/ml. The concentration of FGF-1 is more preferably about 0.5 ng/ml and most preferably about 0.2 ng/ml. IBMX can be included at any effective concentration, and the preferred concentration is less than about 50 μM, more preferably about 40 μM.

The phorbol ester in this composition can be any phorbol ester known to activate protein kinase C, including PMA, TPA, phorbol 12,13-dibutyrate, and phorbol 12,13-diacetate. Preferably PMA is included. However, it is also contemplated that other protein kinase C activators, either a phorbol ester or not, can be included in this composition.

The composition can further comprise EGF, BMP-2, BDNF and/or FGF-2. Preferably BMP-2 is included, and more preferably both BMP-2 and BDNF are included.

Also provided are cultures of neural cells prepared by any aspect of the present invention. Preferably, at least about 25% of the neurons in the culture are TH positive.

Another aspect of the present invention provides a method of treating or ameliorating a disease or condition associated with catecholamine deficiency in a mammal, comprising administering to the mammal an effective amount of fibroblast growth factor 1 (FGF-1), a protein kinase A activator, and a protein kinase C activator. More preferably, dopamine and/or L-DOPA, or the derivative of dopamine and/or L-DOPA, is also administered to the mammal. These therapeutic agents can be administered via any route of administration. However, the agents are preferably administered to the brain of the mammal, more preferably to a ventricle or striatum in the brain, and most preferably to the subventricular zone. In addition, EGF, BMP-2 and/or BDNF can also be administered to the mammal prior to or concurrently with the other agents.

The disease or condition is preferably selected from the group consisting of Alzheimer's disease, Parkinson's disease, Tourette's syndrome, schizophrenia, and clinical depression.

The agents can be administered by any method established in the art, particularly injection or infusion. The agents can be administered separately, in combination, or in a cocktail that includes all the agents to be administered. The agents, particularly the cocktail, can be administered more than once.

Another aspect of the present invention provides pharmaceutical composition comprising fibroblast growth factor 1 (FGF-1), a protein kinase A activator, a protein kinase C activator, dopamine/L-DOPA, and a pharmaceutically acceptable exicipient and/or carrier. The pharmaceutical composition may further comprise EGF and/or BMP-2 and/or BDNF.

DETAILED DESCRIPTION OF THE INVENTION

The present invention provides a method of preparing neurons which express the enzyme tyrosine hydroxylase (TH) in vitro by culturing neural stem cells in the presence of FGF-1, forskolin, dopamine, phorbol ester and isobutyl-methylxanthine. Surprisingly, only low levels of FGF-1 and forskolin were required to efficiently produce TH positive neurons from fetal or adult neural stem cells. Other protein kinase A activators or protein kinase C activators can also be used.

In addition, the present invention also provides a method of inducing dopamine neurons in vivo by administering to a mammal a TH cocktail comprising FGF-1, phorbol ester, forskolin and IBMX. Preferably, the TH cocktail is administered to treat a disease or condition which is associated with dopamine neuron loss or dysfunction. As is the case in vitro, other protein kinase A activators or protein kinase C activators can also be used.

Prior to describing the invention in further detail, the terms used in this application are defined as follows unless otherwise indicated.

Definitions

A "TH positive neuron", or "TH expressing neuron", is a neuron which expresses the tyrosine hydroxylase enzyme. A TH expressing neuron is typically identified by immunostaining with an antibody against tyrosine hydroxylase according to the method described in the present application or other well known methods in the art.

A "dopamine neuron" or "dopaminergic neuron" is a neuron that can produce and secret dopamine.

A "neural stem cell" is a stem cell in the neural cell lineage. A stem cell is a cell which is capable of reproducing itself. In other words, when a stem cell divides, at least some of the resulting daughter cells are also stem cells. The neural stem cells of the present invention, and their progeny, are capable of differentiating into all the cell types in the neural cell lineage, including neurons, astrocytes and oligodendrocytes (astrocytes and oligodendrocytes are collectively called glia or glial cells). Therefore, the neural stem cells are multipotent neural stem cells. The adult neural stem cells of the present invention preferably refer to the neural stem cells located in or derived from the subventricular zone (SVZ) of the forebrain of adult mammals.

"L-DOPA", as used herein, refers to 3-(3,4-dihydroxyphenyl)-L-alanine, its derivatives that can be processed in vivo to dopamine, or the salts thereof. Exemplary derivatives include, but are not limited to, the methyl and hydroxy derivatives of 3-(3,4-dihydroxyphenyl)-L-alanine.

"Dopamine" as used herein as an ingredient of a composition used to produce TH positive neurons, refers to 2-(3, 4-Dihydroxyphenyl)ethylamine, its derivatives that can bind to the dopamine receptor, or the salts thereof. Exemplary derivatives include, but are not limited to, the methyl and hydroxy derivatives of 2-(3,4-Dihydroxyphenyl)ethylamine.

"Dopamine/L-DOPA" refers to dopamine, L-DOPA, or a combination of dopamine and L-DOPA.

A mammalian "non-embryonic" neural stem cell is a neural stem cell located in or derived from a mammal that is not an embryo.

An "adult neural stem cell" is a neural stem cell located in an adult or derived from adult brain tissues. Similarly, an "adult neural cell" is a neural cell located in an adult or derived from an adult neural stem cell.

A "neurosphere" is a group of cells derived from a single neural stem cell as the result of clonal expansion.

A "mammal" is any mammalian animal, preferably a primate, rodent, canine or feline, more preferably a human, dog or cat, and most preferably a human.

An "effective concentration" of an agent is a concentration sufficient to achieve the purpose of the agent in the particular circumstances. For example, the effective concentration of forskolin for TH positive neuron production in the present invention is any concentration of forskolin which, in combination with other agents in the particular culture medium, can induce the production of TH positive neurons from neural stem cells.

"Treating or ameliorating" means the reduction or complete removal of the symptoms of a disease or medical condition.

An "effective amount" is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

Production of TH Positive Neurons in Culture

A culture of neural stem cells were prepared from embryonic or adult mice, and incubated in a TH culture medium containing FGF-1, IBMX, forskolin, PMA and dopamine (Examples 1 and 2). Neurons were produced from both the embryonic and adult neural stem cells, and up to 45% of the neurons derived from embryonic neural stem cells were TH positive neurons.

Surprisingly, the present invention demonstrates that a low concentration of FGF-1 or forskolin is sufficient to induce TH positive neurons. It has previously been reported that various culture media induced TH positive neurons from E13 striatal neurons in a dose dependent manner (Du et al., 1997a; 1997b; 1995; 1994; Stull et al., 1996). Maximal induction was achieved at 10 ng/ml FGF-1, 250 $\mu$M IBMX, 10 $\mu$M forskolin, 200 nM TPA and 20 $\mu$M dopamine (Du et al., 1997a). To induce a meaningful amount of TH positive neurons above the base line, more than 3 $\mu$M of forskolin was required (Du et al., 1997a). However, we used 1 $\mu$M forskolin in the present invention to induce 45% TH positive neurons (Example 1). Our FGF-1 concentration was also substantially lower. We routinely used 0.2 ng/ml FGF-1 in all experiments, while the previous reports typically used 20 ng/ml, 100 fold higher than our concentration. Therefore, the present invention provides an unexpectedly efficient method of producing TH positive neurons.

Other protein kinase A activators can be used in the place of IBMX and/or forskolin. As shown in Example 3, pituitary adenylate cyclase activating polypeptide (PACAP) can be used in the place of forskolin to result in even more TH positive cells than forskolin. Therefore, various proteins kinase A activators may be employed.

The protein kinase A activators may activate protein kinase A directly or indirectly. Direct protein kinase A activators include, but are not limited to, cAMP, cAMP analogs and the salt thereof. Indirect protein kinase A activators may, for instance, increase the concentration of cAMP, thereby activating protein kinase A indirectly. In turn, cAMP concentrations can be increased by a variety of mechanisms, such as by activating adenylate cyclase (e.g., by forskolin or PACAP), or by inactivating cAMP phosphodiesterase (e.g. by IBMX). The effective concentration of each of these activators, alone or in combination, may be determined empirically according to this disclosure and/or established methods in the art. It is preferable to use a combination of protein kinase A activators that work by different mechanisms to increase the efficiency of activation. For example, it is preferable to use a combination of IBMX with cAMP and/or an adenylate cyclase activator to achieve an additive or synergistic effect.

Although we used PMA in the TH culture media, other activators of the protein kinase C pathway may be employed instead of or in addition to PMA. Both direct and indirect protein kinase C activators are useful in the present invention. Protein kinase C activators are well known in the literature and include, without being limited to, TPA, PMA, phorbol 12,13-dibutyrate, phorbol diacetate, phorbol, sapintoxin D, resiniferatoxin, thymeleatoxin, indolactam V, bryostatin-1, mezerein, tinyatoxin, thapsigargin and 1,2-dioctanoyl-sn-glycerol. The effective concentration of each of these agents alone or in combination may vary, and can be determined empirically.

In addition to embryonic neural stem cells, the present invention also provides a method of preparing TH positive neurons from non-embryonic, particularly adult, neural stem cells. It was previously believed that a narrow window of time existed at around E13 during which TH positive neurons can be induced to form (Du et al., 1997a). However, we successfully produced TH positive neurons from neural stem cells of adult animals (Example 2). Accordingly, syngeneic TH positive neurons may be produced for a mammal, particularly an adult mammal, who suffers a disease or condition which can be treated by transplanting TH positive neurons, and the transplantation can be performed without having to suppress the immune system for rejection concerns.

Maximal production of TH positive neurons occurred about 48 hours after the addition of the TH culture medium. Thereafter, the percentage of TH positive neurons decreased over time and dropped to 0.1% of total cells after 6 days in the same TH culture medium. However, when half of the TH culture medium was replenished with fresh medium daily, the decrease in TH positive neurons slowed down, and 2% of the total cells remained TH positive after 6 days in the TH culture medium. Therefore, the factors and agents in the TH culture medium are important not only to induce the commitment of catecholamine neurons, but also to maintain the continued expression of TH. Accordingly, it is preferable to replenish at least some of the TH culture medium when producing TH positive neurons, and more preferably at least half of the medium is replenished daily.

Production of Dopamine Neurons In Vivo

The factors useful in inducing TH positive cells in vitro are also useful in inducing dopamine neurons in vivo. Example 4 illustrates that infusion of a TH cocktail comprising FGF-1, PMA, IBMX and forskolin in the presence of L-DOPA induced production of dopamine neurons in the brain of animals which suffered from lesions associated with dopamine neuron deficiency. Furthermore, the level of dopamine neuron production was correlated with improvements in the lesions. Therefore, the present invention provides a method of treating diseases or conditions which are associated with dopamine neuron loss or dysfunction, such as Alzheimer's disease, Parkinson's disease, Tourette's syndrome, schizophrenia, and clinical depression.

It should be noted that although the therapeutic agents of the present invention, e.g., FGF-1, IBMX, forskolin, PMA and L-DOPA, may be administered as a cocktail, each agent may also be administered separately or in combination with one or more other agents. The effective amount of each agent may vary depending on, for example, the amount of other therapeutic agents, nature and size of the recipient, and the route of administration.

Compositions

The present invention provides compositions that can be used to produce TH positive neurons. The compositions comprise FGF-1, at least one protein kinase A activator, at least one protein kinase C activator, and dopamine/L-DOPA. The protein kinase A activator is preferably cyclic AMP (or its analogs), forskolin, IBMX, PACAP, or any combination thereof. The protein kinase C activator is preferably a phorbol ester, more preferably PMA or TPA, and most preferably PMA.

If a combination of IBMX and forskolin is used for producing TH positive neurons in vitro, the concentration of forskolin is preferably less than about 3 $\mu$M, more preferably about 2 $\mu$M, and most preferably about 1 $\mu$M. The concentration of FGF-1 is preferably less than about 1 ng/ml, more preferably less than about 0.5 ng/ml and most preferably about 0.2 ng/ml.

Pharmaceutical compositions are also provided, comprising FGF-1, at least one protein kinase A activator, and at least one protein kinase C activator. Preferably, dopamine and/or L-DOPA is also included. The protein kinase A activator is preferably cyclic AMP (or its analogs), forskolin, IBMX, PACAP, or any combination thereof. The protein kinase C activator is preferably a phorbol ester, more preferably PMA or TPA, and most preferably PMA.

The pharmaceutical compositions can be delivered via any route known in the art, such as parenterally, intrathecally, intravascularly, intramuscularly, transdermally, subcutaneously, intranasally, or intraperitoneally. Preferably, the composition is delivered into the central nervous system by injection or infusion. Most preferably it is delivered into a ventricle of the brain, particularly the lateral ventricle. For administration into the brain, L-DOPA is preferred over dopamine since L-DOPA crosses the blood brain barrier more readily. It should be noted, however, that the therapeutic agents may be administered separately by different routes. As shown in Example 4, L-DOPA was delivered intraperitoneally, while the remaining agents were delivered in a cocktail to the brain.

The pharmaceutical compositions can be prepared by mixing the desired therapeutic agents with an appropriate vehicle suitable for the intended route of administration. In making the pharmaceutical compositions of this invention, the therapeutic agents are usually mixed with an excipient, diluted by an excipient or enclosed within such a carrier which can be in the form of a capsule, sachet, paper or other container. When the pharmaceutically acceptable excipient serves as a diluent, it can be a solid, semi-solid, or liquid material, which acts as a vehicle, carrier or medium for the therapeutic agent. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the therapeutic agents, soft and hard gelatin capsules, suppositories, sterile injectable solutions, and sterile packaged powders.

Some examples of suitable excipients include artificial cerebral spinal fluid, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the therapeutic agents after administration to the patient by employing procedures known in the art.

For preparing solid compositions such as tablets, the therapeutic agent is mixed with a pharmaceutical excipient to form a solid preformulation composition containing a homogeneous mixture of a compound of the present invention. When referring to these preformulation compositions as homogeneous, it is meant that the therapeutic agents are dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein. The compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

Another formulation employed in the methods of the present invention employs transdermal delivery devices ("patches"). Such transdermal patches may be used to provide continuous or discontinuous infusion of the therapeutic agent of the present invention in controlled amounts. The construction and use of transdermal patches for the delivery of pharmaceutical agents is well known in the art. See, for example, U.S. Pat. No. 5,023,252, herein incorporated by reference. Such patches may be constructed for continuous, pulsatile, or on demand delivery of pharmaceutical agents.

Other suitable formulations for use in the present invention can be found in *Remington's Pharmaceutical Sciences*.

Further provided are TH positive cells produced according to the present invention. These cells are useful for transplantation treatments, particularly to subjects harboring Alzheimer's disease, Parkinson's disease, Tourette's syndrome, schizophrenia, and clinical depression.

The following examples are offered to illustrate this invention and are not to be construed in any way as limiting the scope of the present invention.

EXAMPLES

In the examples below, the following abbreviations have the following meanings. Abbreviations not defined have their generally accepted meanings.

| | | |
|---|---|---|
| ° C. | = | degree Celsius |
| hr | = | hour |
| min | = | minute |
| µM | = | micromolar |
| mM | = | millimolar |
| M | = | molar |
| ml | = | milliliter |
| µl | = | microliter |
| mg | = | milligram |
| µg | = | microgram |
| FBS | = | fetal bovine serum |
| DTT | = | dithiothrietol |
| SDS | = | sodium dodecyl sulfate |
| PBS | = | phosphate buffered saline |
| DMEM | = | Dulbecco's modified Eagle's medium |
| α-MEM | = | α-modified Eagle's medium |
| β-ME | = | β-mercaptoethanol |
| EGF | = | epidermal growth factor |
| PDGF | = | platelet derived growth factor |
| BMP-2 | = | bone morphogenic protein 2 |
| BDNF | = | brain-derived neurotrophic factor |
| FGF-1 | = | fibroblast growth factor 1 |
| FGF-2 | = | fibroblast growth factor 2 |
| IBMX | = | isobutylmethylxanthine |
| PACAP | = | pituitary adenylate cyclase activating polypeptide |
| PMA | = | phorbol 12-myristate 13-acetate |
| TPA | = | 4-β-12-O-tetradecanoylphorbol 13-acetate |
| L-DOPA | = | 3-(3,4-dihydroxyphenyl)-L-alanine |

Example 1

Induction of TH Expressing Neurons from Embryonic Neural Stem Cells

Neural stem cells were prepared from E14 medial and lateral ganglionic eminences and cultured in a culture medium (MHM) containing 20 ng/ml EGF to form neurospheres. The composition of MHM is as follows:

DMEM/F12 (1:1)

glucose (0.6%)

glutamine (2 mM)

sodium bicarbonate (3 mM)

HEPES (5 mM)

insulin (25 µg/ml)

transferrin (100 µg/ml)

progesterone (20 nM)

putrescine (60 µM)

selenium chloride (30 nM)

Seven days later, the neurospheres were passaged by mechanical dissociation and reseeded as single cells (passage 1). After cultured for seven days, the passage 1 neurospheres were completely dissociated and plated on poly-L-ornithine coated glass coverslips in the following medium:

MHM

BDNF (50 ng/ml)

BMP2 (50 ng/ml)

24 hours later, a TH cocktail was added to the media to the following final concentrations:

FGF-1 (0.2 ng/ml)

isobutylmethylxanthine (IBMX, 40 µM)

forskolin (1 µM)

phorbol 12-myristate 13-acetate (PMA, 12.5 nM)

dopamine (20 μM)

At various times after addition of the TH cocktail, the cells were fixed and stained for β-tubulin (a neuron marker) and TH. In the control experiment in which the cells received no TH cocktail, no TH positive cells were observed. In contrast, after two days of incubation in the TH medium, a significant number of cells expressed TH. Thus, 45% of the β-tubulin positive cells, or 7% of total cells, were TH positive. These results indicate that the TH cocktail is effective in inducing TH neuron production.

Maximal TH cell production was observed at 2 days after addition of the TH cocktail. Thereafter, the number of TH positive cells decreased dramatically if the culture was left in the original TH medium. For example, only 0.1% of the total cells was TH positive after being incubated for 6 days in the original TH medium. However, we discovered that if the culture medium was replenished every day, more neurons remained TH positive. Thus, when half of the medium was replaced with the same volume of fresh TH medium daily, 2% of the cells remained TH positive after 6 days in the TH medium, which is 20 fold higher than the 0.1% without medium replenishment. Thus, the present invention also provides a method of prolonging the presence of TH positive cells.

Example 2

Induction of TH Expressing Neurons from Adult Neural Stem Cells

Neural stem cells from adult brain were prepared from the subventricular zone of adult female CD 1 mice as described in Example 1. Thereafter, these stem cells were cultured to form neurospheres, passaged, plated on poly-L-ornithine coated glass coverslips, and incubated in TH medium as described in Example 1. After a two day incubation in the TH medium, 28% of β-tubulin positive cells expressed TH. Therefore, the neural stem cells derived from adult brain were also capable of differentiating into TH positive neurons in response to the TH cocktail.

Example 3

The Effect of PACAP

Another protein kinase A activator, pituitary adenylate cyclase activating polypeptide (PACAP) was also tested in lieu of forskolin in the TH cocktail. Thus, a culture of neural stem cells was prepared and exposed to an TH cocktail as described in Example 1, except that 2 nM PACAP (American Peptide Company, Sunnyvale, Calif.) was used in the place of forskolin. The TH cocktail was replenished by 50% everyday for 4 days, and the cells were stained and counted as described in Example 1. A control experiments using 1 μM forskolin and no PACAP was performed in parallel as a comparison.

The results are summarized below:

TABLE 1

The Effects of Forskolin and PACAP

| | TH Cocktail 1 (Forskolin) | TH Cocktail 2 (PACAP) |
|---|---|---|
| Neurons (% of total cells) | 19% | 23% |
| TH (% of total cells) | 2% | 6.4% |
| TH (% of neurons) | 10.5% | 27.8% |

Therefore, PACAP is effective in the production of TH positive neurons in the present invention. In fact, for the concentrations shown above, PACAP is more effective than forskolin. These results thus indicate that various protein kinase A activators can be used to produce TH positive cells.

Example 4

In Vivo Infusion of TH Cocktail

Six week-old male mice received a unilateral complete 6-hydroxydopamine (6-OHDA) lesion by injecting into each mouse 1 μl of 6-OHDA-HBr (4 μg/μl in 0.2 mg/ml ascorbic acid in 0.9% sterile saline) unilaterally into the substantia nigra and middle forebrain bundle (AP-3.0, L 1.3, DV-3.8; AP-2.5, L 0.8, DV-4.2). Two weeks later, the animals were examined using the apomorphine-induced rotation test (von Voigtlander et al., 1972) to determine the severity of the lesion. As 50 turns/10 minutes is an indicator of dopamine depletion, the animals which showed less than 50 turns in 10 minutes were omitted. Four animals had sufficiently severe lesions and proceeded to the infusion experiments.

The next day, EGF (33 μg/ml) and BDNF (150 μg/ml) were infused into the lateral ventricle of dopamine depleted animals using an osmotic pump (ALZA 2001D) for 7 consecutive days at a flow rate of 0.5 μl/hr. After the infusion, the osmotic pump was removed, and a TH cocktail was infused into the lateral ventricle or striatum using a new osmotic pump for 7 consecutive days. The TH cocktail included the following:

| | |
|---|---|
| FGF-1 | 280 ng/ml |
| PMA | 1.75 μM |
| IBMX | 150 μM |
| forskolin | 700 μM |

The animals also received 10 mg/kg body weight of methyl-L-DOPA into the peritoneum every 2 days during the infusion of the TH cocktail and for 14 days thereafter.

When both TH cocktail and methyl-L-DOPA treatments were completed, the mice received the apomorphine-induced rotation test. Two of four animals displayed a 40% reduction in rotations. The animals were sacrificed the next day and processed for TH immunocytochemistry. The two animals which showed improvement in the apomorphine-induced rotation had 20–30 TH-immunoreactive neurons per section on the infused side of the brain, which correspond to many hundreds of total new dopamine neurons. The two animal which did not show improved rotational behavior had significantly fewer TH neurons, likely due to inefficient infusions. These results provide the first evidence that a TH cocktail can induce new dopamine neurons in vivo in a manner correlated with improved behavior after a dopamine lesion.

We claim:

1. A composition useful for producing TH positive neurons from neural stem cells, comprising fibroblast growth factor 1 (FGF-1), a protein kinase A activator selected from the group consisting of isobutylmethylxanthine (IBMX), pituitary adenylate cyclase activation polypeptide (PACAP), forskolin, and any combination thereof, a phorbol ester, and dopamine/L-DOPA, with the proviso that if the protein kinase A activator is a combination of isobutylmethylxanthine (IBMX) and forskolin, the concentration of forskolin is less than about 3 μM.

2. The composition of claim 1 wherein the protein kinase A activator is a combination of IBMX and forskolin, and the concentration of forskolin is about 1 μM.

3. The composition of claim 1 wherein the concentration of FGF-1 is less than about 1 ng/ml.

4. The composition of claim 1 that comprises dopamine.

5. The composition of claim 1 that comprises L-DOPA.

6. The composition of claim 1 wherein the protein kinase A activator is a combination of IBMX and forskolin, and the concentration of forskolin is about 2 µM.

7. The composition of claim 1 wherein the concentration of FGF-1 is less than about 0.5 ng/ml.

8. The composition of claim 1 wherein the concentration of FGF-1 is about 0.2 ng/ml.

9. The composition of claim 1 wherein the protein kinase A activator is IBMX having a concentration less than about 50 µM.

10. The composition of claim 1 wherein the phorbol ester is one or more selected from the group consisting of 4-β-12-O-tetradecanoylphorbol 13-acetate (TPA), phorbol 12-myristate 13-acetate (PMA), phorbol 12,13-dibutyrate, and phorbol 12,13-diacetate.

11. The composition of claim 10 wherein the phorbol ester is PMA.

12. The composition of claim 1 that comprises FGF-1, forskolin, IBMX, a phorbol ester, and dopamine/L-DOPA.

13. The composition of claim 1 that comprises FGF-1, IBMX, forskolin, PMA, and dopamine.

14. The composition of claim 1 that comprises an amount of FGF-1, a phorbol ester, forskolin, IBMX, and dopamine/L-DOPA effective to produce TH positive neurons from embryonic or adult neural stem cells.

15. The composition of claim 1 further comprising FGF-2, epidermal growth factor (EGF), bone morphogenic protein 2 (BMP-2) and/or brain derived neurotrophic factor (BDNF).

16. The composition of claim 1 comprising a pharmaceutically acceptable excipient and/or carrier.

17. The composition of claim 2 comprising a pharmaceutically acceptable excipient and/or carrier.

18. A method for producing tyrosine hydroxylase (TH) positive neurons from neural stem cells, comprising:
    (a) providing at least one mammalian non-embryonic neural stem cell;
    (b) contacting the neural stem cell with an effective amount of the composition of claim 1; and
    (c) allowing the neural stem cell to differentiate into TH positive neurons.

19. The method of claim 18 wherein the phorbol ester is 4-β-12-O-tetradecanoylphorbol 13-acetate (TPA) or phorbol 12-myristate 13-acetate (PMA).

20. The method of claim 18 wherein the neural stem cell is provided as a culture derived from the subventricular zone of an adult brain.

21. The method of claim 18 wherein the neural stem cell is located in the brain of a mammal.

22. The method of claim 18 further comprising contacting the neural stem cell with epidermal growth factor (EGF) and/or brain-derived neurotrophic factor (BDNF).

23. A method for producing tyrosine hydroxylase (TH) positive neurons from neural stem cells in vitro, comprising:
    (a) providing a culture of neural stem cells;
    (b) incubating the neural stem cells in a TH culture medium comprising the composition of claim 1; and
    (c) allowing the neural stem cells to produce TH positive neurons.

24. The method of claim 23 wherein the protein kinase A activator is a combination of IBMX and pituitary adenylate cyclase activating polypeptide (PACAP).

25. The method of claim 23 wherein the protein kinase A activator is a combination of IBMX and forskolin, wherein the concentration of forskolin is about 1 µM.

26. The method of claim 25 wherein the concentration of IBMX is about 40 µM.

27. The method of claim 23 wherein the concentration of FGF-1 is less than about 1 ng/ml.

28. The method of claim 23 wherein the concentration of FGF-1 is about 0.2 ng/ml.

29. The method of claim 23 wherein the TH culture medium further comprises epidermal growth factor (EGF) and/or brain derived neurotrophic factor (BDNF).

30. The method of claim 23 wherein at least half of the TH culture medium in the culture of step (b) is replaced with an equal volume of fresh TH culture medium daily.

31. A method of treating or ameliorating Parkinson's disease in a mammal, comprising administering to the mammal an effective amount of the composition of claim 1.

32. The method of claim 31 wherein the phorbol ester is 4-β-12-O-tetradecanoylphorbol 13-acetate (TPA) or phorbol 12-myristate 13-acetate (PMA).

33. The method of claim 31 wherein the mammal is an adult mammal.

34. The method of claim 31 wherein the administration is performed by infusion.

35. The method of claim 31 wherein the composition is administered into the subventricular zone of the brain.

36. The method of claim 31 wherein the composition is administered more then once.

37. The method of claim 31 further comprising administering epidermal growth factor (EGF) and/or bone morphogenic protein 2 (BMP-2) and/or brain-derived neurotrophic factor (BDNF) to the mammal.

38. A pharmaceutical composition comprising fibroblast growth factor 1 (FGF-1), a protein kinase A activator selected from the group consisting of isobutylmethylxanthine (IBMX), pituitary adenylate cyclase activating polypeptide (PACAP), forskolin, and any combination thereof; a phorbol ester, dopamine/L-DOPA, and one or more selected from the group consisting of epidermal growth factor (EGF), bone morphogenic protein 2 (BMP-2) and brain derived neurotrophic factor; and a pharmaceutically acceptable excipient and/or carrier with the proviso that if the protein kinase A activator is a combination of isobutylmethylxanthine (IBMX) and forskolin, the concentration of forskolin is less than about 3 µM.

* * * * *